United States Patent
Närhi et al.

(10) Patent No.: US 7,527,804 B2
(45) Date of Patent: May 5, 2009

(54) METHOD FOR IMPROVEMENT OF SOFT TISSUE ATTACHMENT AND IMPLANTS MAKING USE OF SAID METHOD

(75) Inventors: Timo Närhi, Turku (FI); Hannu Paldan, Helsinki (FI); Antti Yli-Urpo, Littoinen (FI); Timo Peltola, Turku (FI); Mika Jokinen, Turku (FI); Risto-Pekka Happonen, Raisio (FI)

(73) Assignee: Vivoxid Oy, Turku (FI)

( * ) Notice: Subject to any disclaimer, the term of this patent is extended or adjusted under 35 U.S.C. 154(b) by 593 days.

(21) Appl. No.: 10/476,157

(22) PCT Filed: Apr. 25, 2002

(86) PCT No.: PCT/FI02/00345

§ 371 (c)(1),
(2), (4) Date: Oct. 27, 2003

(87) PCT Pub. No.: WO02/087648

PCT Pub. Date: Nov. 7, 2002

(65) Prior Publication Data

US 2004/0132603 A1  Jul. 8, 2004

Related U.S. Application Data

(60) Provisional application No. 60/286,587, filed on Apr. 27, 2001.

(51) Int. Cl.
*A61F 2/00* (2006.01)
(52) U.S. Cl. .................................................. 424/423
(58) Field of Classification Search ........................ None
See application file for complete search history.

(56) References Cited

U.S. PATENT DOCUMENTS 4,171,544 A * 10/1979 Hench et al. ............. 623/23.62

(Continued)

FOREIGN PATENT DOCUMENTS

EP   0 401 793   12/1990

(Continued)

OTHER PUBLICATIONS

Jokinen et al (1998) "Influence of sol and surface properties on in vitro bioactivity of sol-gel derived TiO2 and TiO2- SiO2 films deposited by dip-coating method", J. Biomed. Mater. Res., 42, p. 295-302.*

(Continued)

*Primary Examiner*—M P Woodward
*Assistant Examiner*—Bethany Barham
(74) *Attorney, Agent, or Firm*—James C. Lydon

(57) ABSTRACT

A method for improving soft tissue attachment which includes the steps of coating a surface of a material, to which surface soft tissue is to be attached, with a coating rich in $TiO_2$ and/or $SiO_2$, and applying the coating where soft tissue attachment is desired. An implant in which a surface or surfaces of the implant intended to be attached to soft tissue are coated with a porous coating rich in $TiO_2$ and/or $SiO_2$, and the use of a porous surface coating rich in $TiO_2$, $SiO_2$, or $TiO_2$ and $SiO_2$, for the manufacture of an implant for soft tissue attachment are also disclosed.

24 Claims, 4 Drawing Sheets

U.S. PATENT DOCUMENTS

| | | | |
|---|---|---|---|
| 4,330,891 A | 5/1982 | Branemark et al. | 3/1 |
| 4,871,366 A | 10/1989 | Von Recum et al. | 623/11 |
| 5,477,864 A | 12/1995 | Davidson et al. | 128/772 |
| 5,480,438 A | 1/1996 | Arima et al. | 623/16 |
| 6,054,400 A * | 4/2000 | Brink et al. | 501/63 |
| 6,183,255 B1 * | 2/2001 | Oshida | 433/201.1 |
| 2004/0086661 A1 | 5/2004 | Yli-Urpo et al. | 427/595 |
| 2004/0115240 A1 | 6/2004 | Narhi et al. | 424/426 |

FOREIGN PATENT DOCUMENTS

| | | | |
|---|---|---|---|
| WO | WO 86/06617 | | 11/1986 |
| WO | WO 97/45367 | * | 12/1997 |
| WO | WO 00/72777 | * | 12/2000 |

OTHER PUBLICATIONS

Shirkhandzadeh, M. "Nanoporous alkoxy-derived titanium oxide coating" Journal of Material Science: Materials in Medicine, 9 (1998) p. 355-362.*

Shirkhandzadeh et al "Immobilization of calcium phosphate nanoclusters into alkoxy-derived TiO2 coatings" Journal of Material Science: Materials in Medicine, 8 (1997) p. 595-601.*

Holgers et al., "Titanium in Soft Tissues," *Titanium in Medicine* 514-560 (2001).

* cited by examiner

METHOD FOR IMPROVEMENT OF SOFT
TISSUE ATTACHMENT AND IMPLANTS
MAKING USE OF SAID METHOD

This application is a U.S. National stage of International application PCT/FI02/00345, filed Apr. 25, 2002, and which claims priority of U.S. provisional application No. 60/286,587, filed Apr. 27, 2001.

FIELD OF INVENTION

The present invention relates to a method for improving soft tissue attachment using a coating as well as implants making use of said method.

BACKGROUND OF THE INVENTION

Several surface treatments have been developed in order to improve bone bonding of different biomaterials. In experimental animals hydroxyapatite (HA) coatings have been found to improve and speed up the formation of bone bonding. Therefore, the goal of most surface treatments has been to create HA on the materials' surfaces.

Firm bond between the implanted biomaterial and the surrounding soft tissue is, in many cases, far more important than improved bone bonding. A connective tissue capsule normally forms around the implanted materials within a few days. Thickness of the capsule varies depending on the material in question and the stage of healing. Epithelial lining separates all the implanted devices that penetrate skin or mucosa from the soft tissue components that are anatomically normal to the tissues in that area. A direct bond between the implant and soft tissues would be beneficial for several medical devices (e.g. dental implants, canyls, stents, external fixation pins). Until now no methods have been developed that can guarantee firm and safe integration between an implant and the soft tissues.

OBJECT AND SUMMARY OF THE INVENTION

One object of the present invention is to provide a method for improving soft tissue attachment.

Another object of the present invention is to provide an implant with improved soft tissue attachment.

A third object of the present invention is to provide a new use, i.e. use for improved soft tissue attachment of a porous coating rich in $TiO_2$ and/or $SiO_2$.

Thus according to one aspect the invention concerns a method for improving soft tissue attachment comprising the steps of coating a surface of a material, to which surface soft tissue is to be attached, with a coating rich in $TiO_2$ and/or $SiO_2$, and applying said coating wherein soft tissue attachment is desired.

According to another aspect the invention concerns an implant wherein a surface or surfaces of said implant intended to be attached to soft tissue are coated with a porous coating rich in $TiO_2$ and/or $SiO_2$.

According to a third aspect the invention concerns the use of a porous surface coating rich in $TiO_2$, $SiO_2$, or $TiO_2$ and $SiO_2$, for the manufacture of an implant for soft tissue attachment to said coating.

DETAILED DESCRIPTION OF THE INVENTION

Figure 1:
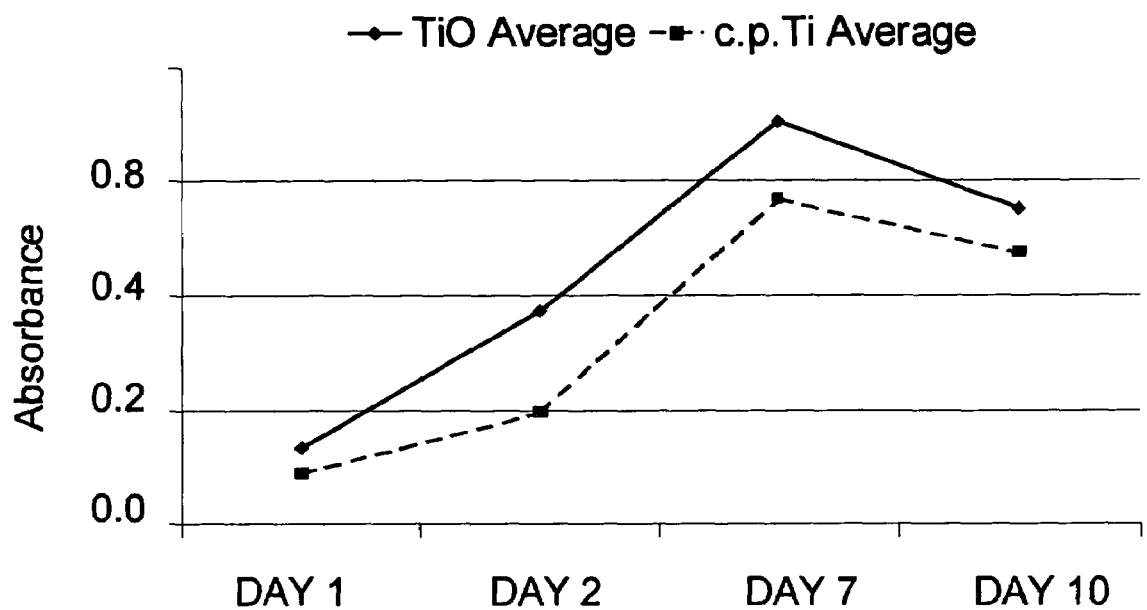
FIG. 1 shows a fibroblast proliferation curve after seeding cells on a $TiO_2$ coated and non-coated commercially pure (c.p.) Ti surface. Cell proliferation is significantly higher on the coated Ti surface already after three days when compared to c.p. Ti.
Figure 2:
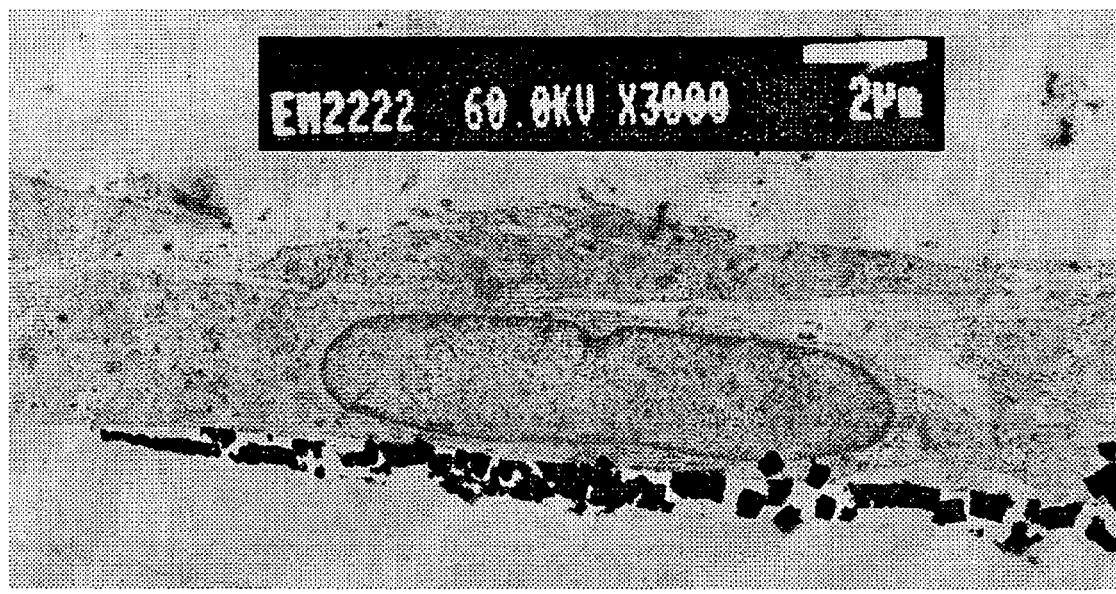
FIG. 2 shows a transmission electron microscope (TEM) image of fibroblasts seeded on a $TiO_2$ coated and non-coated c.p. Ti surface. Cells seeded on coated Ti show more flattened morphology compared to cells on c.p. Ti indicating good bonding between the cell membrane and coated Ti surface. Focal adhesion nodules can clearly be seen (black arrows) in cells grown on coated Ti surface.
Figure 3:
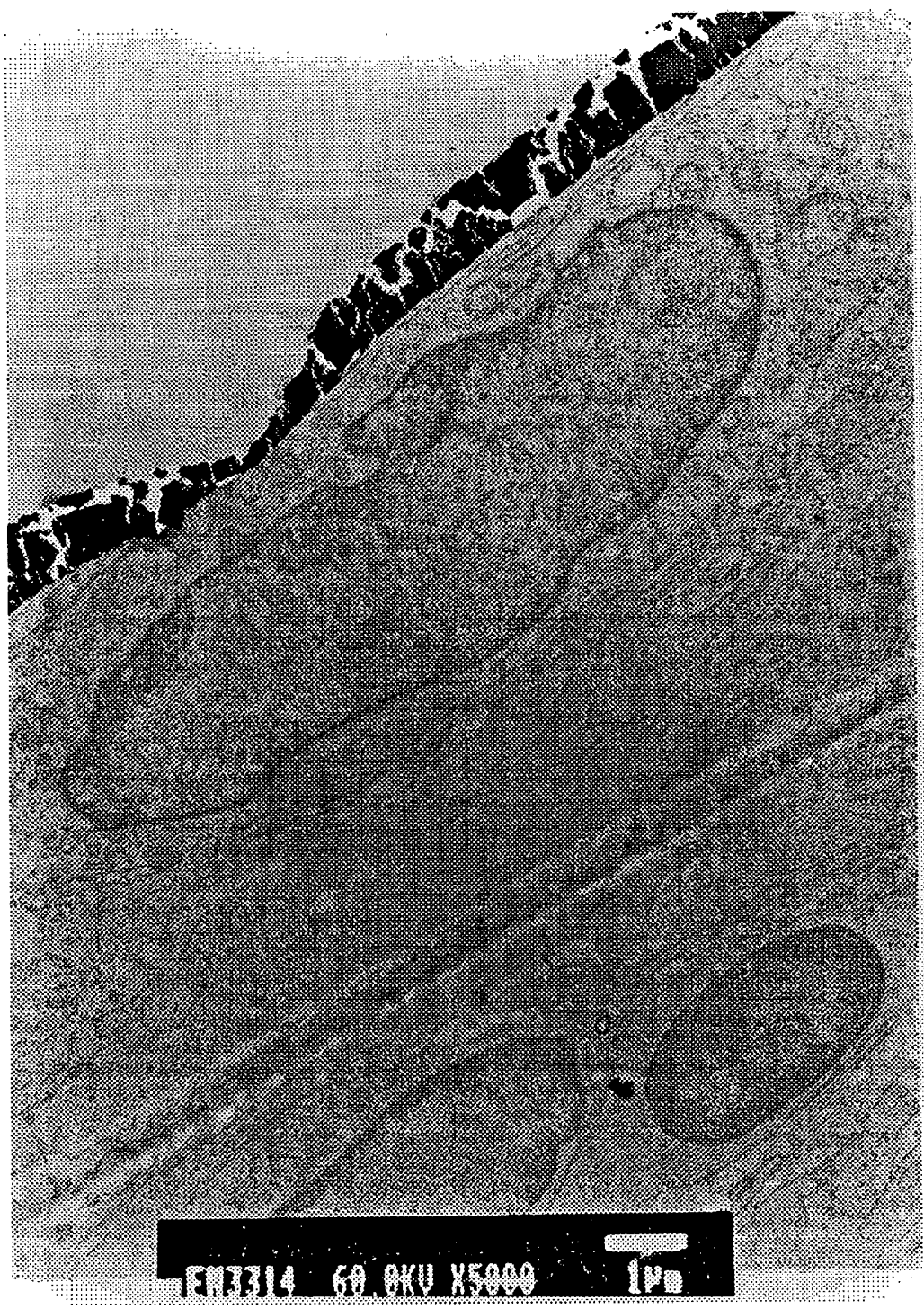
FIG. 3 shows a TEM image of subcutaneous soft tissue cells attached on a $TiO_2$ coated c.p. Ti surface. The coating remains attached on tissue surface after removing the implant. No capsule formation can be seen.
Figure 4:
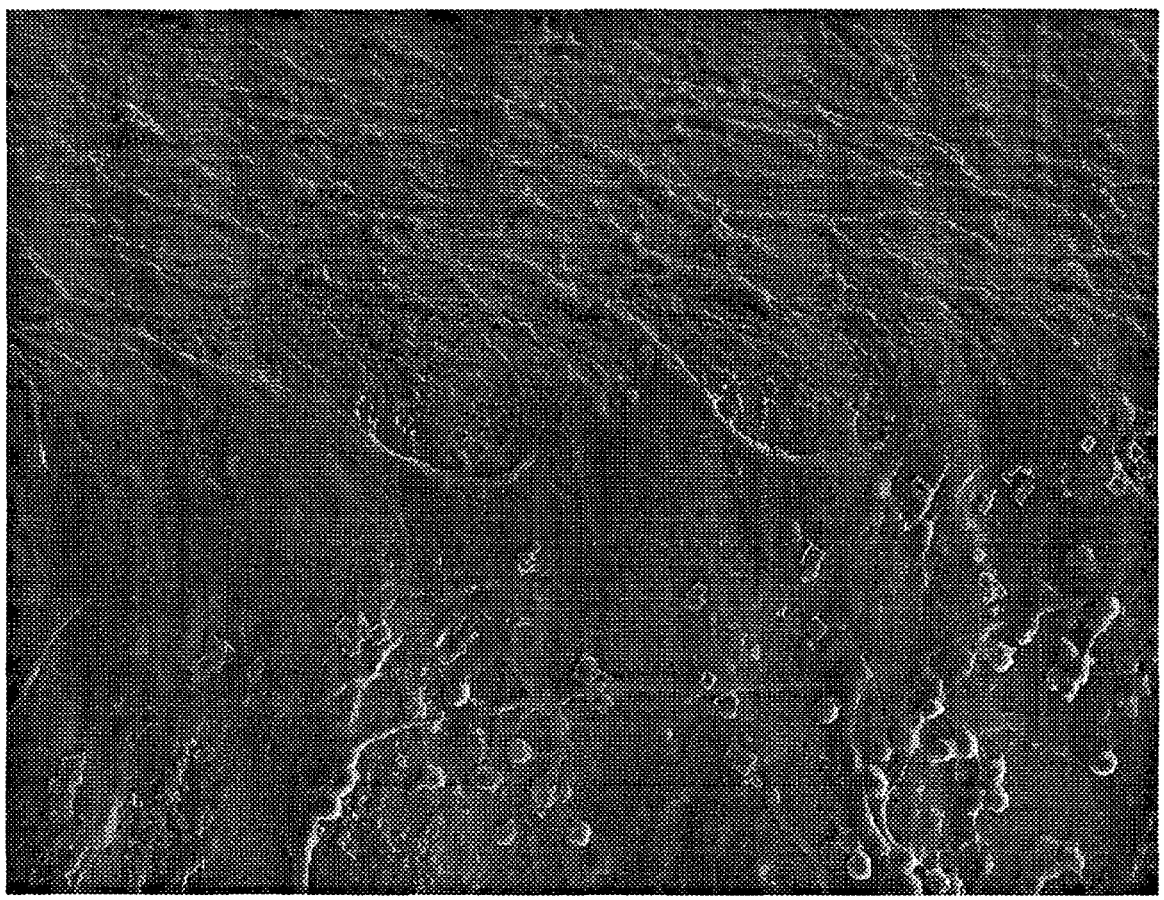
FIG. 4 shows fibroblasts and collagen bundles on a $TiO_2$-gel coated c.p. Ti disc after 7 days of implantation in rat subcutaneous surrounding. The extracellular matrix is firmly attached on $TiO_2$ coated surface.
Figure 5A:
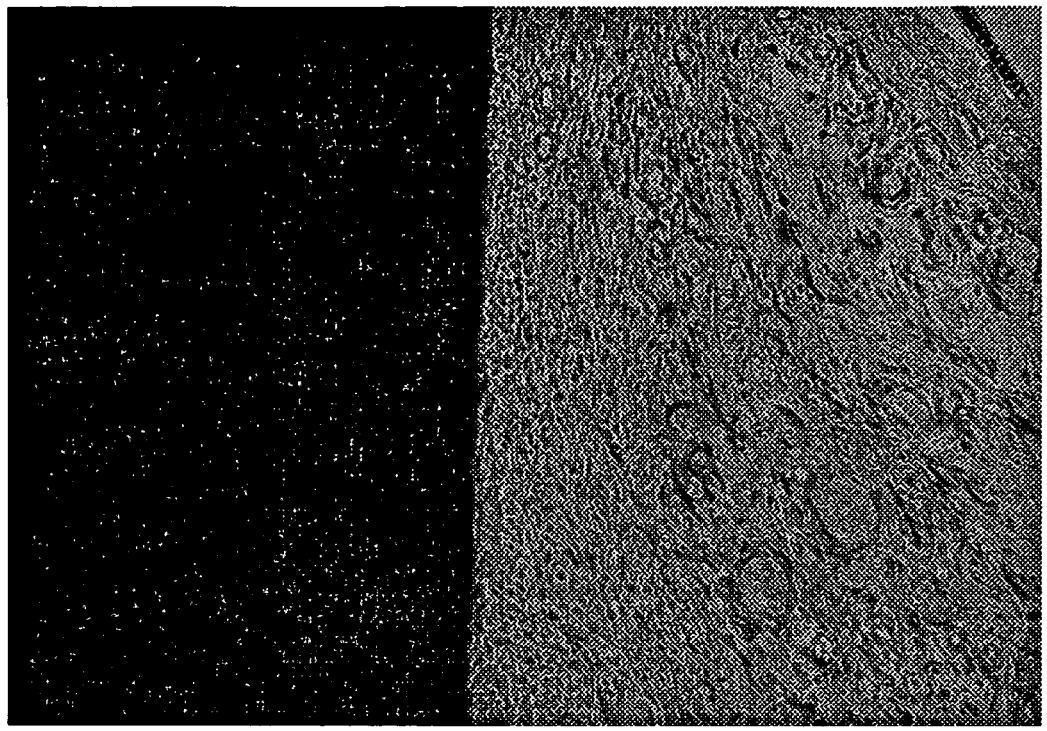
FIGS. 5a and 5b show routine light microscopy images of a $TiO_2$-gel coated c.p. Ti disk (5a) and an non-coated disc (5b) after 8 days of subcutaneous implantation in rat. Soft tissue is firmly attached to a $TiO_2$-gel coated Ti surface without an intervening connective tissue capsule. Capsule formation is clearly seen on c.p. Ti surface.
Figure 5B:
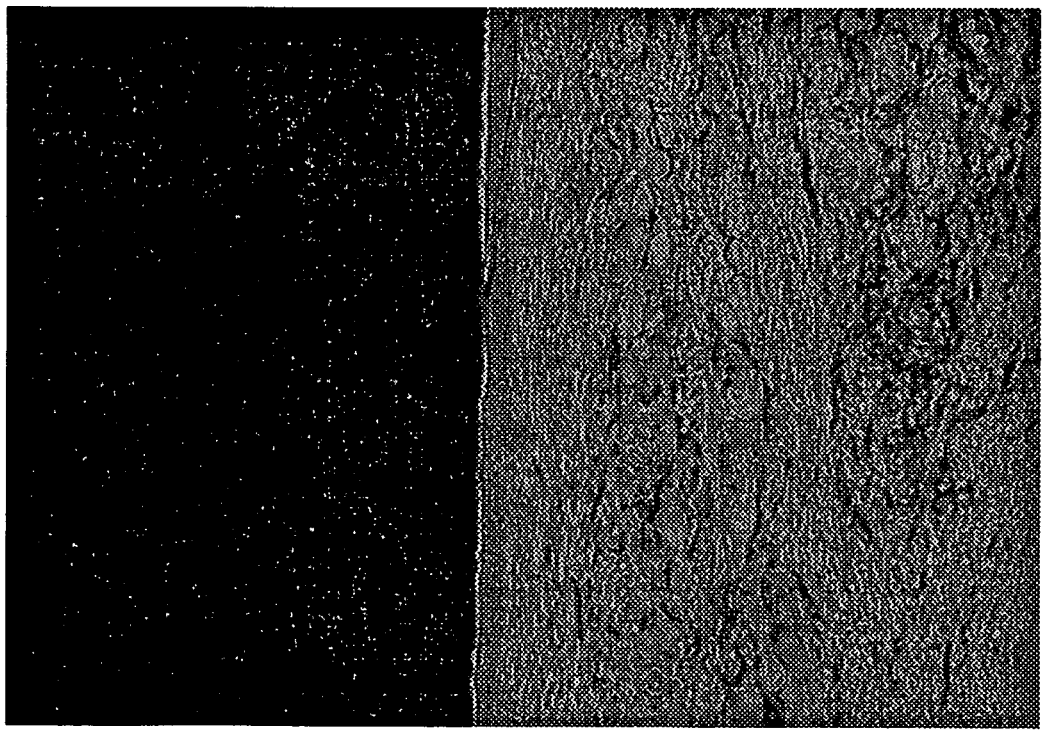

"Biomedical application" in the context of this application is meant to be understood in a broad context. Thus both in vivo and in vitro applications are included.

The term "soft tissue" refers to all mammalian tissues except mineralizing hard tissues. Soft tissues include e.g. subcutaneous and cutaneous connective tissue, musculoskeletal connective tissues, muscle, epithelia, mucosa and nerve tissue.

"Soft tissue attachment" refers in the context of this application to good bonding between coated material and surrounding soft tissues without an intervening connective tissue capsule.

Reference to "a coating rich in $TiO_2$ and/or $SiO_2$" means that an essential part of the coating is $TiO_2$ and/or $SiO_2$. Typically more than 50 wt-% of the composition of the coating is $TiO_2$ and/or $SiO_2$. Preferably more than 70 wt-% of the composition of the coating is $TiO_2$ and/or $SiO_2$ and most preferably more than 90 wt-%.

The term "implant" in the contest of this application refers to any device that is meant to at least partially be inserted into a mammal including humans for a period lasting at least long enough for soft tissue attachment to take place.

The term "biocompatible" means compatible with the other ingredients of the coated material and not deleterious to the recipient thereof.

The term "tissue defect" refers to any site or locus being deficient in soft tissue components anatomically normal to the site of the body of said mammal.

The present invention provides a method for improving soft tissue attachment comprising the steps of coating a surface of a material, to which surface soft tissue is to be attached, with a coating rich in $TiO_2$ and/or $SiO_2$ (or other metallic oxide, e.g. $TaO_2$ or $ZrO_2$), and applying said coating wherein soft tissue attachment is desired. Highly preferable, if not essential, to the invention is that the coating is porous. Typically the coating comprises pores with a diameter and/or depth of less than 50 nm. Preferably an essential part of the pores of the coating consist of pores having a diameter of 2 to 50 nm and a depth of at least 1 nm. The material to be coated is typically selected from the group consisting of titanium, nitinol, ceramic and polymer material and any combination thereof.

The method preferably comprises the steps of a) preparing a $TiO_2$, $SiO_2$ or $TiO_2$-$SiO_2$ sol;

b) aging said sol;

c) contacting a surface to which soft tissue is to be attached with said sol which sol has been prepared in step a) and aged in step b) wherein said contacting is optionally carried out by dipping said surface into said sol;

d) withdrawing said surface from said sol at a predetermined speed to obtain a coated surface if said contacting of step c) has been carried out by dipping said surface into said sol;

e) optionally heat treating the coated surface for a predetermined time;

f) optionally cleaning the coated surface;

g) optionally drying the coated surface;

h) repeating at least steps c) and d), but optionally also any of steps a) to g), a number of times to obtain the desired number of layers of coating if more than one layer of coating is desired; and j) applying said surface where soft tissue attachment is desired.

The sol can be a $TiO_2$ sol, a $SiO_2$ sol and/or a $TiO_2$-$SiO_2$ sol. The preparation of the sol typically comprises the steps of (i) dissolving tetraisopropyl orthotitanate $Ti((CH_3)_2CHO)_4$ and/or tetraethylorthosilicate in ethanol; (ii) dissolving ethyleneglycol monoethylether ($C_2H_5OCH_2CH_2OH$), deionised water, and hydrochloric acid or nitric acid in ethanol; (iii) mixing solutions obtained in step (i) and (ii) and optionally stirring said mixture efficiently.

The sol is typically at a chilled temperature of −10 to +20° C., preferably −5 to +5° C. and most preferably −2 to +2° C. during step c). The sol prepared in step a) is aged in step b) for 1 min to 10 days, preferably for 1 to 48 hours. The surface can be contacted with the sol by dipping it into the sol in step c) and it is typically withdrawn in step d) from the sol at a speed of 0.01 mm/s to 10 mm/s, preferably at a speed of 0.1 mm/s to 1.0 mm/s. Contacting of the surface with the sol can alternatively be carried out by other means such as spraying or condensing.

The surface is typically heat treated in step e) at a temperature of 20 to 630° C., Heat treatment is preferably carried out at a temperature of 30 to 45° C. if e.g. the coating additionally comprises heat labile components such as bioactive agents. Heat treatment can also be carried out at higher temperatures depending on the thermal properties of the coated material. Temperature ranges preferable for some materials are 90 to 160° C. and 250 to 630° C. The duration of the heat treatment can vary. The heat treatment in step e) is typically carried out for 0.1 s to 10 d, preferably for 1 s to 10 h and most preferably for 1 min to 1 h. The higher the heat treatment temperature the less likely a long heat treatment would be preferable.

The coating or coatings obtained are typically cleaned in step f) and preferably cleaning is carried out ultrasonically.

Alternatively a preferred method for preparing a coating for improved soft tissue attachment according to the invention comprises the steps of a) preparing a simulated body fluid;

b) adding a dissolving Si-source and/or Ti-source to the simulated body fluid prepared in step a);

c) contacting a surface to which soft tissue is to be attached with the mixture obtained in step b) wherein said contacting is optionally carried out by dipping said surface into said mixture;

d) letting dissolving $SiO_2$-based and/or $TiO_2$-based material form a coating as it is adsorbed and/or reprecipitated onto the surface of said material; and e) applying said surface wherein soft tissue attachment is desired.

A typical Si-source is bioactive glass or sol-gel derived $SiO_2$. The simulated body fluid of step a) is a solution that mimics the body fluid or a solution buffered to body fluid pH, i.e. pH 7.2-7.4.

A preferrable simulated body fluid (SBF) is prepared by dissolving reagent chemicals of NaCl, $NaHCO_3$, KCl, $K_2HPO_4.3H_2O$, $MgCl_2.6H_2O$, $CaCl_2.2H_2O$ and $Na_2SO_4$ into deionised water. The fluid is buffered at physiological pH 7.40 at 37° C. with tris(hydroxymethyl)aminomethane and hydrocloric acid. The resulting liquid emulates the inorganic composition of the body fluid providing the ion concentrations as follows: 142.0 mM $Na^+$, 5.0 mM $K^+$, 1.5 mM $Mg^{2+}$, 2.5 mM $Ca^{2+}$, 147.8 mM $Cl^-$, 4.2 mM $HCO_3^-$, 1.0 mM $HPO_4^{2-}$ and 0.5 mM $SO_4^{2-}$.

The consistence of a simulated body fluid can slightly vary. It can e.g. comprise 1.0-1.5 mM of $Mg^{2+}$, 1.6-2.5 mM of $Ca^{2+}$, 103-147.8 mM of $Cl^-$ and/or 4.2-27 mM of $HCO_3^-$.

The present invention further provides an implant wherein a surface or surfaces of said implant intended to be attached to soft tissue are coated with a coating rich in $TiO_2$ and/or $SiO_2$. The coating is typically porous comprising pores with a diameter of less than 50 nm and preferably an essential part of the pores of the coating consists of pores having a diameter of 2 to 50 nm and a depth of at least 1 nm. The material of the implant to be coated typically is titanium, tantalum, zirconium, nitinol, ceramic and polymer material or any combination thereof.

The coating of the implant is obtainable using a method comprising the steps of a) preparing a $TiO_2$, $SiO_2$ or $TiO_2$-$SiO_2$ sol;

b) optionally aging said sol;

c) contacting a surface to which soft tissue is to be attached with said sol which sol has been prepared in step a) and aged in step b) wherein said contacting is optionally carried out by dipping said surface into said sol;

d) withdrawing said surface from said sol at a predetermined speed to obtain a coated surface if said contacting of step c) has been carried out by dipping said surface into said sol;

e) optionally heat treating the coated surface for a predetermined time;

f) optionally cleaning the coated surface;

g) optionally drying the coated surface; and h) repeating at least steps c) and d), but optionally also any of steps a) to g), a number of times to obtain the desired number of layers of coating if more than one layer of coating is desired.

Alternatively the coating is obtainable using a method comprising the steps of a) preparing a simulated body fluid;

b) adding a dissolving Si-source to the simulated body fluid prepared in step a);

c) contacting a surface to which soft tissue is to be attached with the mixture obtained in step b) wherein said contacting is optionally carried out by dipping said surface into said mixture; and d) letting the dissolving $SiO_2$-based material form a coating as it is adsorbed and/or reprecipitated onto the surface of said material.

Other typical, preferred or most preferred features of the surface coating of the implant are the same as those defined above for the method if applicable for the surface coating of the implant.

The present invention additionally provides use of a surface coating rich in $TiO_2$, $SiO_2$, or $TiO_2$ and $SiO_2$, for the manufacture of an implant for soft tissue attachment to said coating. The coating is typically porous comprising pores with a diameter of less than 50 nm and preferably an essential part of the pores of the coating consist of pores having a diameter of 2 to 50 nm and a depth of at least 1 nm. The material of the implant to be coated typically is titanium, nitinol, ceramic and polymer material or any combination thereof.

Other typical, preferred or most preferred features of the surface coating to be used are the same as defined above for the method and/or implant coating if applicable for the use.

The present invention thus relates to surface treatment of a material, e.g. metal, ceramic or polymer material, that permits soft tissue attachment via $TiO_2$ and/or $SiO_2$ rich coatings. $OH^-$ groups of $TiO_2$ and/or $SiO_2$ coatings promote, e.g. by binding fibronectin glycoprotein, mammal connective tissue cell (fibroblasts) chemotaxis, migration, and adhesion on the material surfaces. In percutaneous devices this facilitates direct attachment of fibroblast-like cells on SiOH or TiOH coated surfaces preventing epithelial cells from proliferating between the soft tissue components and the implanted material. In subcutaneous devices soft tissues attach on the coated material surfaces without an intervening connective tissue capsule. Alternatively a coating or coatings can promote the attachment of epithelial layers of organs and endothelium and reepithelization of skin wounds. Coatings can be used to conduct nerve regeneration.

A sol-gel dip-coating method is one way to create uniform multi-layer bioactive coatings on the surface of the implants. By this method inorganic oxide ceramics can be prepared from colloidal and polymeric sols. It gives the flexibility to control different properties of the resulting ceramics, like composition, surface area, porosity, adsorption capacity, dissolution rate, etc. Different sol-gel-derived titania and silica coatings can be prepared by changing the composition and using different aging time for sols, changing heat-treatment temperature and number of coating layers. Furthermore, the surface properties (OH-groups, nanoscale topography and crystallinity) can be changed locally with the help of laser treatment.

The present invention also concerns the use of said coating methods in products intended for treatment of defects of soft tissue, e.g. maxilla, mandible, tooth, root canal, ear, nose, skull, joints, defects in bone and subcutaneous and intradermal soft tissue, e.g. of coatings of implants, external fixation pins, tissue guiding membranes bone augmentation materials, canyls for penetrating skin, stents, vascular implants, valves and breast implants.

The present invention further concerns in vitro applications, such as the use of coatings according to the invention for coating surfaces used for soft tissue animal cell cultures or for coatings of tissue engineering devices.

The present invention provides a biologically acceptable method, i.e. a sol-gel derived $TiO_2$ or $SiO_2$ coating, that can be made on material (e.g. on metal, polymer, ceramic) surface, which material is implanted into a mammal including humans. Preferably said materials are dipped into $TiO_2$ or $SiO_2$ sol. Different titania and silica coatings can be prepared by changing the composition and using different aging time for sols, changing heat-treatment temperature and number of coating layers.

A coating according to the invention can e.g. be prepared as follows (Peltola, Timo: Nanoscale Dimensions and In Vitro Calcium Phosphate Formation: Studies on Sol-gel-derived Materials and Bioactive Glass. Thesis, University of Turku, Turku, Finland, 2000):

Commercially pure (c.p.) Ti (grade 2) is used as a substrate material. Ti is ground with silicon carbide paper. Commercially available tetraisopropyl orthotitanate $Ti((CH_3)_2CHO)_4$ or tetraethylorthosilicate is dissolved in absolute ethanol (solution I). Ethyleneglycol monoethylether ($C_2H_5OCH_2CH_2OH$), deionised water, and fuming hydrochloric acid (HCl, 37%) or nitric acid is dissolved in ethanol (solution II). Solutions I and II are mixed and efficiently stirred. The ready-made sol is kept at 0° C. in order to slow down the condensation reaction. The sol is kept at 0° C. during the dip-coating process.

After 1 hour or 24 hours of aging, the coating is prepared by dipping the Ti substrate into the sol and then withdrawing it at the speed of 0.30 mm/s. The coated substrates are heat-treated (20-500° C.) for 10 min. After heat-treatment, coatings are cleaned ultrasonically in acetone for 5 min and in ethanol for another 5 min, and finally dried at ambient temperature. This dipping, heating and washing cycle is repeated as many times as needed, depending on the number of desired coating layers. Said sol can optionally contain one or more active or inactive agents such as drugs, mineralising or antimicrobial agents (e.g. bioactive glass, sol-gel derived ceramics), growth factors, preservatives, colouring, flow enhancing, bonding or suspension enhancing agents that will be derived into the final coating. The concentration of the active agents within $TiO_2$ and $SiO_2$ sol remain homogenous during the dipping procedure.

Coatings can also be made biomimetically using an external Si and/or Ti-source e.g. as follows (Jokinen, Mika: Bioceramics by Sol-gel Method, Processing and Properties of Monoliths, Films and Fibers. Thesis, Åbo Akademi University, Turku, Finland, 1999):

Si-sources are in simulated body fluid conditions soluble $SiO_2$-based materials, such as bioactive glasses or sol-gel derived $Sio_2$. A substrate, such as a Ti-implant or a polymer, is put into a solution containing the Si-source, where the dissolving $SiO_2$-based material forms a coating as it is adsorbed and/or reprecipitated onto the substrate surface. The solution is preferably a solution that mimics body fluid, such as SBF or to body fluid pH buffers (pH 7.2-7.4) solutions. The formed coating is able to nucleate hydroxyapatite directly from the same solution as long as the solution contains calcium and phosphate ions (as is the case when using SBF). If the coated substrate has been prepared in buffered solutions (pH 7.2-7.4) that do not contain calcium and phosphate ions or if one desires to enhance the hydroxyapatite formation, the coated substrate can be further moved into another liquid, which contains calcium phosphate ions [such as 1.0-2.0×SBF (ion concentrations multiplied with the coefficient)]. Alternatively, the coatings can be produced on precisely determined areas of the medical devices using laser technique.

$CO_2$ laser operates in the infrared part of the spectra at 10.6 μm. Radiation is absorbed by sol-gel-derived titania or silica gels. The substrate is only heated locally and the coating can be processed selectively, which allows different areas of the same coating to have different properties. It is possible to control the degree of densification of sol-gel-derived coatings by choosing adequate processing parameters like laser power, laser beam transition speed and the size of the spot of the focused laser beam.

By using a computer-controlled motion stage during processing it is possible to produce patterned coatings on medical implants, to coat only certain areas of an implant, as required by some clinical applications. 1 mm thick sheet of c.p. Ti (grade 2) is often used as substrate material. Ti substrate plates are dipped into the sol. Each layer is first heat-treated in a furnace, and thereafter further locally treated with $CO_2$-laser (two 3 mm lanes). Power ranges that can be used are 12-20 W. Distance between two neighboring laser scan lines can be kept at 100 µm. Motion speed can be 2.5 mm/s.

Alternatively $SiO_2$ ceramics can be mixed into polymeric materials that in aqueous environment form Si rich surfaces on the composite materials that function comparably to the coatings described above.

The coatings can be applied on biomaterials used in reconstruction or augmentation of soft tissue structures in a patient in need thereof comprising inserting the coated material into tissue defects or implanting it to cover the anatomic structure in question. The coated materials can either be resorbable or non-resorbable.

Anatomic structures treatable according to the method of this invention include, but are not limited to, maxilla, mandible, tooth, root of a tooth, defects in bone, ear, nose, skull, joints, subcutaneous, percutaneous and intradermal soft tissues or dermal soft tissue.

Preferred $TiO_2$ and $SiO_2$ coatings in the present invention were selected on the basis that: (a) sol-gel coatings can be made in thin layers which makes it possible to coat small devices; (b) bioactive components, e.g. drugs, growth factors, can be added in the coatings; (c) coatings can be applied on porous surfaces and structures.

The following examples are offered as illustrations of the present invention and are not to be constructed as limitations thereof.

EXAMPLE 1

$TiO_2$ coatings are made on percutaneous dental implant abutments as described above. After a sufficient healing period submerged implants are exposed, their cover screws are removed and $TiO_2$ coated Ti abutments are connected to the osseointegrated implants. During soft tissue wound healing connective tissue components attach directly on the coated Ti surface thus preventing the formation of epithelial lining between the implant and surrounding soft tissue components.

EXAMPLE 2

Like example 1 but the coating is applied on the upper portion of a one-stage implant that will be connected directly in the oral cavity without submerging period.

EXAMPLE 3

Like in example 1 but the coating is applied on a fixation pin used for external fracture fixation.

EXAMPLE 4

Like in example 1 but the coating is applied on a percutaneous plastic stent.

EXAMPLE 5

Like examples 1 to 4 but $SiO_2$ or $TiO_2$ coating is applied on the subgingival portion of a polymer, ceramic or metallic crown of a tooth.

EXAMPLE 6

Like examples 1 to 4 except that the coating is applied on a vascular stent.

EXAMPLE 7

Like examples 1 to 4 except that the coating is applied on a heart valve implant material.

EXAMPLE 8

Like examples 1 to 4 except that the coating is applied on breast implant material.

EXAMPLE 9

Like examples 1 to 4 but the coatings will be treated with $CO_2$ laser in order to create tailor made bioactive zones on coated material surfaces

EXAMPLE 10

$SiO_2$ coating is produced on a material surface by immersing the substrate in SBF solution in presence of an external Si ion containing ceramic material such as bioactive glass granules.

It will be appreciated that the present invention can be incorporated in the form of a variety of embodiments, only a few of which are disclosed herein. It will be apparent for the specialist in the field that other embodiments exist and do not depart from the spirit of the invention. Thus, the described embodiments are illustrative and should not be construed as restrictive.

The invention claimed is:

1. A method for improving soft tissue attachment comprising the steps of
    coating a surface of a material, to which surface soft tissue is to be attached, with a coating comprising at least 50 wt-% $TiO_2$ and
    applying said coating wherein soft tissue attachment is desired, wherein soft tissue attachment occurs without formation of a connective tissue capsule for at least 8 days after application,
wherein said coating is porous and comprises pores with a diameter of 2 to 50 nm and a depth of from 1 nm to less than 50 nm and wherein the material to be coated is selected from the group consisting of titanium, nitinol, ceramic and polymer material and any combination thereof.

2. The method of claim 1, wherein said soft tissue attachment occurs in vitro.

3. The method of claim 1, wherein said soft tissue attachment occurs in vivo.

4. The method of claim 3, wherein said in vivo attachment is to a stent.

5. The method of claim 4, wherein said stent is a vascular stent.

6. The method of claim 1, wherein said method comprises the steps of
    a) preparing a $TiO_2$ or $TiO_2$-$SiO_2$ sol;
    b) aging said sol;
    c) contacting a surface to which soft tissue is to be attached with said sol which sol has been prepared in step a) and aged in step b).

7. The method of claim 6, wherein the sol is a $TiO_2$ sol.

8. The method of claim 6, wherein the preparation of the sol comprises the steps of
    i) dissolving tetraisopropyl orthotitanate $Ti((CH_3)_2CHO)_4$ or tetraisopropyl orthotitanate and tetraethylorthosilicate in ethanol, ii) dissolving ethyleneglycol monoethylether ($C_2H_5OCH_2CH_2OH$), deionised water, and hydrochloric acid or nitric acid in ethanol, iii) mixing solutions obtained in step i) and ii).

9. The method of claim 8, further comprising stirring said mixture.

10. The method of claim 6, wherein the sol is at a chilled temperature of −10 to +20° C. during step c).

11. The method of claim 6, wherein the sol prepared in step a) is aged in step b) for 1 min to 10 days.

12. The method of claim 1, wherein soft tissue is a member selected from the group consisting of subcutaneous connective tissue, cutaneous connective tissue, musculoskeletal connective tissue, muscle, epithelia, mucosa and nerve tissue.

13. The method of claim 6, wherein said contacting is carried out by dipping said surface into said sol and;
    d) withdrawing said surface from said sol at a predetermined speed to obtain a coated surface.

14. The method of claim 13, wherein the surface is contacted with the sol by dipping it into the sol in step c) and withdrawn in step d) from the sol at a speed of 0.01 mm/s to 10 mm/s.

15. The method of claim 13, further comprising
    h) repeating at least steps c) and d) a number of times to obtain a desired number of layers of coating.

16. The method of claim 6, further comprising
    e) heat treating the coated surface for a predetermined time.

17. The method of claim 16, wherein the surface is heat treated in step e) at a temperature of 20 to 630° C.

18. The method of claim 16, wherein the heat treatment in step e) is carried out for 0.1 s to 10 d.

19. The method of claim 6, further comprising
    f) cleaning the coated surface.

20. The method of claim 19, wherein the coating or coatings are ultrasonically cleaned in step f).

21. The method of claim 6, further comprising
    g) drying the coated surface.

22. The method of claim 1, wherein said method comprises the steps of
    a) preparing a simulated body fluid;
    b) adding a dissolving Ti-source to the simulated body fluid prepared in step a);
    c) contacting a surface to which soft tissue is to be attached with the mixture obtained in step b);
    d) letting dissolving $TiO_2$-based material form a coating as it is adsorbed and/or reprecipitated onto the surface of said material; and
    e) applying said surface wherein soft tissue attachment is desired.

23. The method of claim 22, wherein the simulated body fluid of step a) is a solution that mimics the body fluid or a solution buffered to pH 7.2-7.4.

24. The method of claim 22, wherein the simulated body fluid is SBF comprising 1.0-1.5 mM of $Mg^{2+}$, 1.6-2.5 mM of $Ca^{2+}$, 103-147.8 mM of $Cl^{31}$ and 4.2-27 mM $HCO_3^{31}$.

* * * * *